United States Patent [19]

Cesa

[11] Patent Number: 5,118,846
[45] Date of Patent: Jun. 2, 1992

[54] SYNTHESIS OF N-DISUBSTITUTED AMIDES BY REACTION OF AMIDES WITH CERTAIN ORGANIC HYDROXYL COMPOUNDS

[75] Inventor: Mark C. Cesa, South Euclid, Ohio

[73] Assignee: The Standard Oil Company, Cleveland, Ohio

[21] Appl. No.: 515,913

[22] Filed: Apr. 27, 1990

[51] Int. Cl.$^5$ .......................................... C07C 231/12
[52] U.S. Cl. ..................... 564/215; 564/153; 564/159; 564/201; 564/203; 564/204; 564/207; 564/218; 564/219; 564/182; 564/183; 564/184; 554/68
[58] Field of Search ............... 564/153, 159, 201, 203, 564/215, 204, 207, 218, 219, 182, 183, 184, 215; 260/404

[56] References Cited

U.S. PATENT DOCUMENTS

| | | | |
|---|---|---|---|
| 2,461,509 | 2/1949 | Harvey | 260/558 |
| 3,534,099 | 10/1970 | Cookson et al. | 564/159 |
| 4,322,271 | 3/1982 | Jensen et al. | 564/215 |
| 4,853,485 | 8/1989 | Bellis | 564/215 |
| 5,041,659 | 8/1991 | Cesa et al. | 564/215 |

FOREIGN PATENT DOCUMENTS

| | | | |
|---|---|---|---|
| 48-28417 | 9/1973 | Japan . | |
| 0052260 | 3/1983 | Japan | 564/184 |
| 0016831 | 1/1984 | Japan | 564/159 |
| 0020258 | 2/1984 | Japan | 564/203 |
| 201854 | 9/1987 | Japan . | |
| 789533 | 1/1958 | United Kingdom . | |
| 2092136 | 8/1982 | United Kingdom | 564/218 |

OTHER PUBLICATIONS

J. Chem. Soc., 1962, 5277-5280, Cheesemon et al.
Ceivandov, Zh. Org. Khimu, vol. 19, No. 4, 738-739 (Apr. 1983).
Kashiwagi et al., Nippon Kagaku, Kaishi, 1980 (2), 279-281.
Watanabe, Bull. Chem. Soc. Jap., 16, 2647-2651 (1983).
Weckess et al., Organic Chemistry, John Wiley & Sons pp. 62-63.
Noller, Chemistry of Organic Compound, WB Saunders Co., pp. 234-235.

Primary Examiner—Carolyn Elmore
Attorney, Agent, or Firm—C. S. Lynch; M. F. Esposito; L. W. Evans

[57] ABSTRACT

Disclosed is a method which comprises introducing into a reaction zone a feed which comprises a hydroxyl compound reactant, R"OH at least one amide reactant selected from R—CONH$_2$ and R—CONHR', and a Lewis base as catalyst, thereby reacting R"OH with said amide reactant to produce a reaction mixture containing at least one disubstituted amide selected from R—CONR"$_2$ and R—CONR'R", wherein
each of R, R' and R" contains no acetylenic unsaturation and 1 to 30 carbon atoms;
each of R, R' and R" is selected from a hydrocarbyl groups and a hydrocarbyl group that is substituted with a group selected from carbamoyl, hydrocarbylcarbamoyl, dihydrocarbylcarbamoyl, and hydroxyl.

6 Claims, No Drawings

SYNTHESIS OF N-DISUBSTITUTED AMIDES BY REACTION OF AMIDES WITH CERTAIN ORGANIC HYDROXYL COMPOUNDS

This invention relates to the synthesis of N-disubstituted amides by reaction of amides with certain organic hydroxyl compounds using organic and inorganic bases as catalysts for such reaction.

The important industrial solvent, N,N-dimethylacetamide, is currently prepared industrially from acetic acid and dimethylamine. It is a superior organic solvent, with high boiling range and good thermal stability relative to other amides such as dimethylformamide. The current DMAC synthesis suffers from relatively high raw material costs. As a result, DMAC has a high price (about $1.00 per pound). This high price precludes use of DMAC in many applications where relatively inferior but lower priced solvents are used.

The process of the present invention has the potential to lower N-disubstituted amides production costs substantially because of the much lower prices of the starting materials compared with the price of the raw materials of the current synthetic method, thus offering the potential for growth of DMAC demand into applications where its superior properties would be an advantage.

It is an object of the present invention to improve the process of making N-disubstituted amides.

It is a further object of the invention to lower the cost of making N-disubstituted amides by condensing amides with alcohols in the presence of a Lewis base as catalyst.

Other objects, as well as, aspects and advantages, of the invention will become apparent from a study of the specification, including the specific examples and the claims.

The foregoing and other objects are realized by the present invention according to which there is provided a method which comprises introducing into a reaction zone a feed which comprises a hydroxyl compound reactant, R"OH, at least one amide reactant selected from R—CONH$_2$ and R—CONHR'; and a Lewis base as catalyst, thereby reacting R"OH with said amide reactant to produce a reaction mixture containing at least one disubstituted amide selected from R—CONR"$_2$ and R—CONR'R", wherein each of R, R' and R" contains no acetylenic unsaturation and 1 to 30 carbon atoms, each of R, R' and R" is selected from a hydrocarbyl group and a hydrocarbyl group that is substituted with a group selected from carbamoyl, hydrocarbylcarbamoyl, dihydrocarbylcarbamoyl, and hydroxyl.

Some Lewis base catalysts are ammonia; mono-, di-, and trihydrocarbylamines; heterocyclic nitrogen compounds such as, for example, pyridines, hydroxides of elements of Groups 1 and 2 having atomic weight less than 145; and catalysts of the above description supported on or incorporated into solid organic polymer supports or solid inorganic supports such as silica, alumina, magnesia, kieselguhr, and pumice.

The groups refer to the Periodic Table of the Elements that numbers the groups from 1 to 18, appearing in *Chemical and Engineering News*, Feb. 4, 1985, p. 27.

The hydrocarbylamine catalysts usually used have the formula R$_1$R$_2$R$_3$N, where each of R$_1$, R$_2$, and R$_3$ is independently selected from H, a C$_1$-C$_{12}$ hydrocarbyl group containing no ethylenic or acetylenic unsaturation; and a substituted C$_1$-C$_{12}$ hydrocarbyl group containing no ethylenic or acetylenic unsaturation, where said substituent is a —NR$_4$R$_5$ group, where R$_4$ and R$_5$ are independently selected from H and a C$_1$-C$_4$ alkyl group.

The heterocyclic nitrogen compound catalysts usually used have the formula

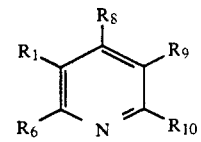

where R$_6$, R$_7$, R$_8$, R$_9$ and R$_{10}$ are each independently selected from H, a C$_1$-C$_{12}$ hydrocarbyl group containing no ethylenic or acetylenic unsaturation; 2-pyridyl; 3-pyridyl; and a substituted C$_1$-C$_{12}$ hydrocarbyl group containing no ethylenic or acetylenic unsaturation, where said substituent is a —NR$_4$R$_5$ group, where R$_4$ and R$_5$ are independently selected from H and a C$_1$-C$_4$ alkyl group.

Optimum catalyst amounts can be determined by routine experiments, but often vary from 0.0001 to 10 moles introduced into the reaction zone per 100 moles of the amide reactant, introduced into the reaction zone. More usually the amount is from 0.01 to 5 moles per 100 moles of the amide reactant.

A variety of acidic catalysts has been reported for N-alkylation of amides with alcohols. H$_2$SO$_4$ is an effective catalyst for condensation of tertiary alcohols (e.g. tert-butyl alcohol) with amides (R. Kh. Geivandov, *Zh. Org. Khim.*, 1983, 19, 738-739; M. T. Harvey, S. Caplan, U.S. Pat. No. 2,461,509). Organic acids (G. W. H. Cheeseman, R. C. Poller, *J. Chem. Soc.*, 1962, 5277-5280), ammonium salts (H. Kashiwagi, S. Enomoto, Nippon Kagaku Kaishi, 1980, 279-281), and zeolites (JP 62 201,854 [Mitsubishi Chem. Ind.]) have also been reported. Particularly effective catalysts for primary alcohols are transition metal salts. For example, oxides, peroxides, sulfides, oxyhalogenates, hydroxides, inorganic salts, or organic salts of copper, silver, gold, zinc, cadmium, mercury, titanium, zirconium, tin, lead, chromium, molybdenum, tungsten, iron, cobalt, nickel, rhodium, palladium, iridium, platinum, or thorium are reported in a patent to Asahi Chemical Industry Co. (S. Senoo, Y. Fukuoka, K. Sasaki, JP 48 28,417); and phosphine-coordinated ruthenium halides are also effective (Y. Watanabe, T. Ohta, Y. Tsuji, *Bull. Chem. Soc. Japan*, 1983, 56, 2647-2651.) The alkylation of amides with alcohols may also be carried out in the absence of catalyst (A. Wolfram, E. Schallus, GB 789,533). There are, however, no known literature or patent references to the use of base catalysts for this amide synthesis reaction.

According to the present invention, the Lewis base catalyzed alkylation of amides with alcohols can be carried out in either the vapor phase or in the liquid phase, at atmospheric pressure or reduced or elevated pressure, in a batch mode, flow mode, or continuous stirred reactor mode.

The presence of inert diluents for any of the starting materials is within the scope of the invention. For example, the use of nitrogen or other inert gas in the reaction zone is permitted, and is favored in high-temperature liquid phase conditions to minimize unwanted side reactions. Also, the use of inert solvents with the reactants such as, for example (but not restricted to), alkanes and aromatic hydrocarbons is within the scope of the invention.

The reactants can be employed from the beginning of the reaction in the full amounts required for the reaction, or the reactants can be introduced to the reaction zone successively or stepwise during the course of the reaction.

The process of this invention can be carried out at from 50° to 600° C. Preferred temperatures range from 100° C. to 500° C.; at lower temperatures the reaction rate is unsuitably low, and at higher temperatures undue amounts of byproducts are formed.

Pressures can range from 0.1 atmosphere to 200 atmospheres or more. In liquid phase runs carried out in pressure vessels with low-boiling reactants, high reaction temperatures required for sufficient reaction rates result in pressures well above 1 atmosphere.

The alcohol/amide starting materials mole ratio can range from 0.1 to 20, but usual ratios range from 1.0 to 10. Lower amounts of alcohol relative to amide result in reduced amide conversion and product yields, and higher amounts can alcoholyze amide products, lowering yield of desired product.

The following examples of the invention are exemplary and should not be taken as in any way limiting.

EXAMPLE 1

A mixture of N-methylacetamide (36.55 g, 0.5000 mol), methanol (32.04 g, 0.9999 mol), pyridine (1.20 g, 0.0152 mol), was placed in a stainless steel autoclave of 300 ml internal volume. The reactor was sealed, and the reaction mixture was purged with nitrogen through a dip tube for 30 minutes. The reactor was then heated to 363° C., and the reaction mixture was stirred vigorously at that temperature for 5 hours. The reactor was then cooled, and the reaction mixture was analyzed by gas chromatography. Conversion of N-methylacetamide was 86.7%. The yield of N,N-dimethylacetamide was 40.2%, corresponding to a selectivity of 46.4%.

COMPARATIVE EXAMPLE A

A mixture of N-methylacetamide (36.57 g, 0.5003 mol) and methanol (32.05 g, 1.0002 mol) was placed in a stainless steel autoclave of 300 ml internal volume. The reactor was sealed, and the reaction mixture was purged with nitrogen through a dip tube for 30 minutes. The reactor was then heated to 363° C., and the reaction mixture was stirred vigorously at that temperature for 5 hours. The reactor was then cooled, and the reaction mixture was analyzed by gas chromatography. Conversion of N-methylacetamide was 85.9%. The yield of N,N-dimethylacetamide was 36.1%, corresponding to a selectivity of 42.0%.

EXAMPLE 2

A mixture of acetamide (29.55 g, 0.5002 mol), methanol (22.04 g, 0.9999 mol), and pyridine (1.20 g, 0.0152 mol) was placed in a stainless steel autoclave of 300 ml internal volume. The reactor was sealed, and the reaction mixture was purged with nitrogen through a dip tube for 30 minutes. The reactor was then heated to 366° C., and the reaction mixture was stirred vigorously at that temperature for 4.5 hours. The reactor was then cooled, and the reaction mixture was analyzed by gas chromatography. Conversion of acetamide was 86.8%. The yield of N,N-dimethylacetamide was 39.3%, corresponding to a selectivity of 45.3%, and the yield of N-methylacetamide was 28.2%, corresponding to a selectivity of 32.4%.

COMPARATIVE EXAMPLE B

A mixture of acetamide (29.54 g, 0.5001 mol) and methanol (32.05 g, 1.0002 mol) was placed in a stainless steel autoclave of 300 ml internal volume. The reactor was sealed, and the reaction mixture was purged with nitrogen through a dip tube for 30 minutes. The reactor was then heated to 364° C., and the reaction mixture was stirred vigorously at that temperature for 4 hours. The reactor was then cooled, and the reaction mixture was analyzed by gas chromatography. Conversion of acetamide was 83.3%. The yield of N,N-dimethylacetamide was 31.7%, corresponding to a selectivity of 38.1%, and the yield of N-methylacetamide was 30.8%, corresponding to a selectivity of 37.0%.

As will be evident to those skilled in the art various modifications of this invention can be made or followed in the light of the foregoing disclosure and discussion without departing from the spirit and scope of the disclosure or from the scope of the claims.

I claim:

1. A method which comprises introducing into a reaction zone a feed which comprises a hydroxyl compound reactant, R"OH, at least one amide reactant selected from R—CONH$_2$ and R—CONHR', and a Lewis base as catalyst, thereby reacting R"OH with said amide reactant to produce a reaction mixture containing at least one disubstituted amide selected from R—CONR"$_2$ and R—CONR'R", wherein each of R, R' and R" contains no acetylenic unsaturation and 1 to 30 carbon atoms, each of R, R', and R" is a hydrocarbyl group wherein said Lewis base catalyst is selected from (1) hydrocarbyl amines R$_1$R$_2$R$_3$N, where each of R$_1$, R$_2$, and R$_3$ is independently selected from: a C$_1$-C$_{12}$ hydrocarbyl group containing no ethylenic or acetylenic unsaturation, and a substituted C$_1$-C$_{12}$ hydrocarbyl group containing no ethylenic or acetylenic unsaturation, where the substituent is a —NR$_4$R$_5$ group, where R$_4$ and R$_5$ are independently selected from C$_1$-C$_4$ alkyl groups, (2) heterocyclic nitrogen compound catalysts having the formula

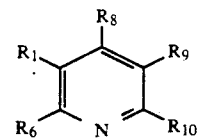

where R$_6$, R$_7$, R$_8$, R$_9$ and R$_{10}$ are each independently selected from: H; a C$_1$-C$_{12}$ hydrocarbyl group containing no ethylenic or acetylenic unsaturation; 2-pyridyl; 30-pyridyl; and a substituted C$_1$-C$_{12}$ hydrocarbyl group containing no ethylenic or acetylenic unsaturation, where the substituent is a —NR$_4$R$_5$ group, where R$_4$ and R$_5$ are as before recited, and (3) hydroxides of elements of Groups 1 and 2 having atomic weights less than 145.

2. A method according to claim 1 wherein R"OH is methanol and said at least one amide is selected from acetamide and N-methylacetamide, thereby reacting methanol with said at least one amide to produce a reaction mixture containing N,N-dimethylacetamide.

3. A method of claim 1 wherein the mole ratio of R"OH to said selected amide(s) introduced into the reaction zone is from 0.1 to 20.

4. A method of claim 3 wherein said mole ratio is from 1 to 10.

5. A method of claim 2 wherein the mole ratio of methanol to said at least one amide introduced into the reaction zone is from 0.1 to 20.

6. A method of claim 5 wherein said mole ratio is from 1 to 10.

* * * * *